United States Patent [19]
Bruce et al.

[11] Patent Number: 6,146,014
[45] Date of Patent: Nov. 14, 2000

[54] METHOD FOR LASER SCANNING FLIP-CHIP INTEGRATED CIRCUITS

[75] Inventors: Victoria J. Bruce; Michael R. Bruce, both of Austin, Tex.

[73] Assignee: Advanced Micro Devices, Inc., Sunnyvale, Calif.

[21] Appl. No.: 09/187,314

[22] Filed: Nov. 4, 1998

[51] Int. Cl.[7] .......................... G01K 11/00; G01N 25/72
[52] U.S. Cl. ................. 374/161; 374/120; 374/4
[58] Field of Search .................. 374/161, 130, 374/4–7, 120

[56] References Cited

U.S. PATENT DOCUMENTS

| | | | |
|---|---|---|---|
| 4,136,566 | 1/1979 | Christensen | 374/161 |
| 4,171,915 | 10/1979 | Hesselink | 356/361 |
| 4,437,761 | 3/1984 | Kroger et al. | 374/161 |
| 4,640,626 | 2/1987 | Schmid et al. | 374/161 |
| 4,664,515 | 5/1987 | Imura et al. | 374/130 |
| 4,683,750 | 8/1987 | Kino et al. | 73/606 |
| 4,770,528 | 9/1988 | Imura et al. | 374/130 |
| 4,840,496 | 6/1989 | Elleman et al. | 374/130 |
| 4,956,538 | 9/1990 | Moslehi | 374/161 |
| 5,246,291 | 9/1993 | Lebeau et al. | 374/5 |
| 5,250,809 | 10/1993 | Nakata et al. | 374/5 |
| 5,430,305 | 7/1995 | Cole, Jr. et al. | 250/559.07 |
| 5,474,381 | 12/1995 | Moslehi | 374/161 |
| 5,479,252 | 12/1995 | Worster et al. | 356/237.5 |
| 5,661,520 | 8/1997 | Bruce | 348/92 |
| 5,683,180 | 11/1997 | Lyon et al. | 374/161 |
| 5,741,070 | 4/1998 | Moslehi | 374/161 |
| 5,803,606 | 9/1998 | Petry et al. | 374/130 |
| 5,820,265 | 10/1998 | Kleinerman | 374/161 |
| 5,971,608 | 10/1999 | Koizumi | 374/5 |
| 5,984,522 | 11/1999 | Koizumi | 374/5 |
| 6,033,107 | 3/2000 | Farina et al. | 374/161 |

OTHER PUBLICATIONS

Kyuma et al., "Fiber–Optic Instrument for Temperature Measurement," IEEE Journal of Quantum Electronics, vol. QE–18, No. 4, Apr. 1982, pp. 676–679.

*Primary Examiner*—Diego Gutierrez
*Assistant Examiner*—Stanley J. Pruchnic, Jr.

[57] ABSTRACT

Methods for analyzing temperature characteristics of an integrated circuit. In one embodiment, a beam of laser light is directed at the back side of an integrated circuit. The intensity level of laser light reflected from the integrated circuit is measured and compared to a reference intensity level. The magnitude of the difference between the reference intensity level and the intensity level of the reflected laser light is indicative of a temperature characteristic of the integrated circuit.

25 Claims, 5 Drawing Sheets

METHOD FOR LASER SCANNING FLIP-CHIP INTEGRATED CIRCUITS

FIELD OF THE INVENTION

The present invention is generally directed to analysis of semiconductor integrated circuits, and more particularly to analysis of a semiconductor integrated circuit using a laser.

BACKGROUND OF THE INVENTION

During manufacture of an integrated circuit, electronic components are formed upon and within a front side surface of a semiconductor structure having opposed front side and backside surfaces. The components are inter-coupled with electrically conductive interconnect lines to form an electronic circuit. Signal lines that are to be connected to external devices are terminated at flat metal contact regions called input/output (I/O) pads. Following manufacture, the integrated circuit, or "chip," is typically secured within a protective semiconductor device package. Each I/O pad of the chip is then connected to one or more terminals of the device package. The terminals of a device package are typically arranged about the periphery of the package. The I/O pads of the chip are electrically connected to the terminals of the device package. Some types of device packages have terminals called "pins" for insertion into holes in a printed circuit board (PCB). Other types of device packages have terminals called "leads" for attachment to flat metal contact regions on an exposed surface of a PCB.

As integrated circuit fabrication technology improves, manufacturers are able to integrate more and more functions onto single silicon substrates. As the number of functions on a single chip increases, however, the number of signal lines that need to be coupled to external devices also increases. The corresponding numbers of required I/O pads and device packages terminals increase as well, as do the complexities and costs of the device packages. Constraints of high-volume PCB assembly operations place lower limits on the physical dimensions of and distances between device package terminals. As a result, the areas of peripheral-terminal device packages having hundreds of terminals are largely proportional to the number of terminals. These larger packages with fine-pitch leads are subject to mechanical damage during handling or testing. Mishandling can result in a loss of lead co-planarity, adversely affecting PCB assembly yields. In addition, the lengths of signal lines from chip I/O pads to device package terminals increase with the number of terminals, and the high frequency electrical performance of larger peripheral-terminal device packages suffers as a result.

Grid array semiconductor device packages have terminals arranged in a two-dimensional array across an underside surface of the device package. As a result, the physical dimensions of grid array device packages having hundreds of terminals are much smaller than their peripheral-terminal counterparts. Such smaller packages are highly desirable in portable device applications such as laptop and palmtop computers and hand-held communications devices such as cellular telephones. In addition, the lengths of signal lines from chip I/O pads to device packages terminals are shorter, thus the high-frequency electrical performances of grid array device packages are typically better than those of corresponding peripheral-terminal device packages. Grid array device packages also allow the continued use of existing PCB assembly equipment developed for peripheral-terminal devices.

Figure 1:
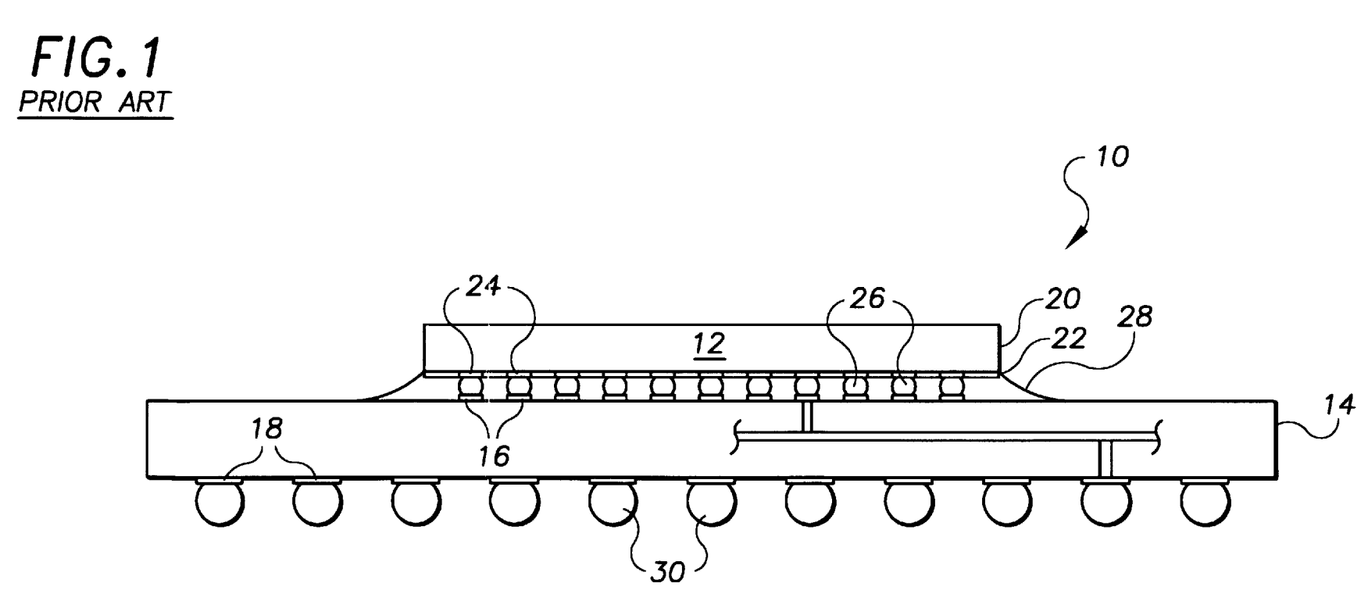
FIG. 1 is a cross-sectional view of an example BGA device.

An increasingly popular type of grid array device package is the ball grid array ("BGA") device package. FIG. 1 is a cross-sectional view of an example BGA device 10. The device 10 includes an integrated circuit 12 mounted upon a larger package substrate 14. Substrate 14 includes two sets of bonding pads: a first set of bonding pads 16 on an upper surface adjacent to integrated circuit 12 and a second set of bonding pads 18 arranged in a two-dimensional array across an underside surface. Integrated circuit 12 includes a semiconductor substrate 20 having multiple electronic components formed within a circuit layer 22 upon a front side surface of semiconductor substrate 20 during wafer fabrication. The electronic components are connected by electrically conductive interconnect lines to form an electronic circuit. Multiple I/O pads 24 are also formed within circuit layer 22. I/O pads 24 are typically coated with solder to form solder bumps 26.

The integrated circuit is attached to the package substrate using the controlled collapse chip connection method, which is also known as the C4® or flip-chip method. During the C4 mounting operation, solder bumps 26 are placed in physical contact with corresponding members of the first set of bonding pads 16. Solder bumps 26 are then heated long enough for the solder to reflow. When the solder cools, I/O pads 24 of integrated circuit 12 are electrically and mechanically coupled to the corresponding members of the first set of bonding pads 16 of the package substrate. After integrated circuit 12 is attached to package substrate 14, the region between integrated circuit 12 and package substrate 14 is filled with an under-fill material 28 to encapsulate the C4 connections and provide additional mechanical benefits.

Package substrate 14 includes one or more layers of signal lines that connect respective members of the first set of bonding pads 16 and the second set of bonding pads 18. Members of the second set of bonding pads 18 function as device package terminals and are coated with solder, forming solder balls 30 on the underside surface of package substrate 14. Solder balls 30 allow BGA device 10 to be surface mounted to an ordinary PCB. During PCB assembly, BGA device 10 is attached to the PCB by reflow of solder balls 30 just as the integrated circuit is attached to the package substrate.

The C4 mounting of integrated circuit 12 to package substrate 14 prevents physical access to circuit layer 22 for failure analysis and fault isolation. Thus, new methods and systems for analyzing flip-chips are desirable.

SUMMARY OF THE INVENTION

The present invention, in various embodiments, is a method for analyzing temperature characteristics of an integrated circuit. In one embodiment, a beam of laser light is directed at the back side of an integrated circuit. The intensity level of laser light reflected from the integrated circuit is measured and compared to a reference intensity level. The magnitude of the difference between the reference intensity level and the intensity level of the reflected laser light is indicative of a temperature characteristic of the integrated circuit.

In another embodiment, a reference intensity level is established from the laser light reflected from a first integrated circuit. A second intensity level is established from laser light reflected from a second integrated circuit. The two intensity levels are then compared, whereby magnitude of the difference between the intensity levels is indicative of a temperature characteristic of the integrated circuit.

Yet another method for analyzing temperature characteristics of an integrated circuit comprises: (a) scanning a first integrated circuit with a beam of laser light, the first integrated circuit being in a state in which no power is applied; (b) measuring a first intensity level of laser light reflected from the first integrated circuit; (c) supplying voltage and current to the first integrated circuit; (d) running a selected series of test vectors on the first integrated circuit; (e) measuring a second intensity level of laser light reflected from the first integrated circuit; and (f) establishing a delta value of the difference between the first and second intensity levels. Steps (a)–(f) are then repeated using a second integrated circuit instead of the first integrated circuit. The delta value of the first integrated circuit is compared to the delta value of the second integrated circuit, whereby a magnitude of the difference indicates a temperature characteristic of the second integrated circuit relative to the first integrated circuit.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood upon consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of semiconductor structures and system for laser analysis thereof. The invention may be particularly advantageous for laser analysis of flip-chip semiconductor structures. While the present invention is not so limited, an appreciation of various aspects of the invention is best gained through a discussion of various example applications described below.

The invention provides a method and system for analyzing temperature characteristics of an integrated circuit. In one embodiment, the invention may be used to identify areas of a circuit that generate excessive heat. Such areas may be indicative of defective portions of the integrated circuit and may be the result of slight, undesired variances in the fabrication process.

The example embodiments of the invention generally use reflected laser light to measure the heat generated by areas of an integrated circuit. In one example mode, laser light is directed at the backside surface of a reference integrated circuit having a circuit layer disposed near the front side. A fixed focus laser detector is positioned for detection of laser light reflected from the reference integrated circuit, and the focus is fixed at the circuit layer in order to detect the intensity level of reflected laser light. The reference semiconductor structure may be, for example, an integrated circuit known to be functional. Laser light is then directed at the integrated circuit to be analyzed, and the intensity of the reflected laser light is measured. Where the difference in intensity levels is greater than some predetermined level, there may be a defect in the circuit at the corresponding location.

Figure 2:
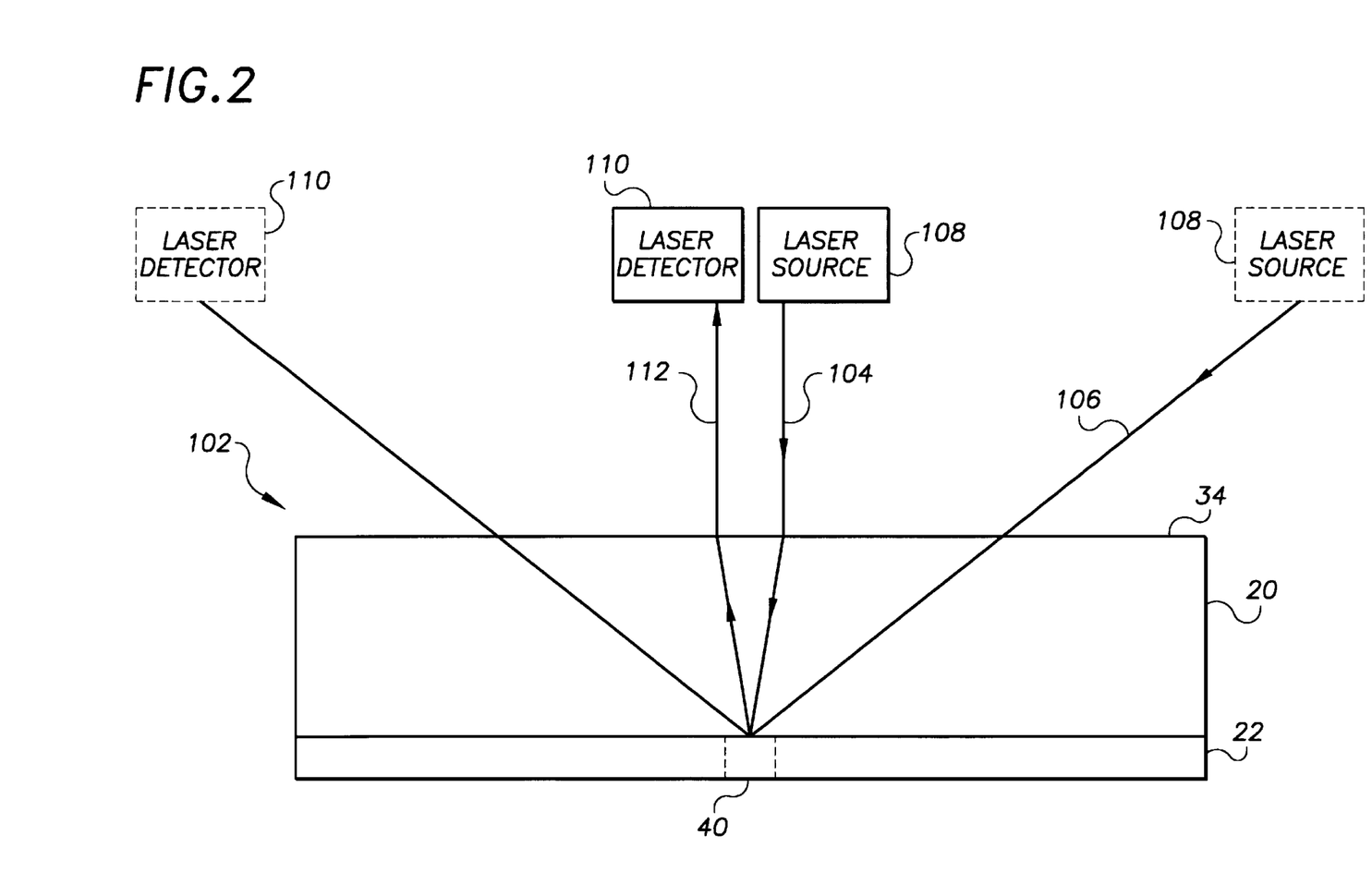
FIG. 2 is a cross-sectional view of a portion of a reference semiconductor structure on which backside laser analysis can be performed.

FIG. 2 is a cross-sectional view of a portion of a semiconductor structure on which backside laser analysis can be performed. The structure 102 is a reference integrated circuit that is scanned with a laser for the purpose of establishing a reference level to which to compare a reflected laser intensity level taken from an integrated circuit to be analyzed. Two alternative angles of incidence of a beam of laser light are illustrated. Beam 104 strikes the backside surface 34 of substrate 20 at an angle that is substantially perpendicular thereto. Alternatively, beam 106 strikes the backside surface of substrate 20 at an angle of between about 30° to 45°. Laser scanning at the angle of beam 106 provides an increased optical path length through the silicon, thereby providing more interaction between the laser and silicon and a larger shift in the index of refraction.

A laser source 108 produces electromagnetic radiation in the form of, for example, a beam of laser light 104. The difference in the index of refraction of air and that of the substrate 20 bends the beam 104 toward the component 40. When photons of the beam 104 strike electronic components, for example, component 40, the beam is reflected back toward the backside surface 34.

A laser detector 110 is positioned to receive reflected laser beam 112. Laser detector 110 is focused on the reflection of beam 112 reflected from component 40 when the circuit is at a starting temperature, for example, room temperature.

In an example embodiment, the laser beam is scanned across the back side surface 34 of the substrate, and the laser detector 112 detects intensity levels of the reflected beam at selected locations. The intensity levels and the associated locations are provided to a control unit (not shown) and stored for subsequent reference.

Figure 3:
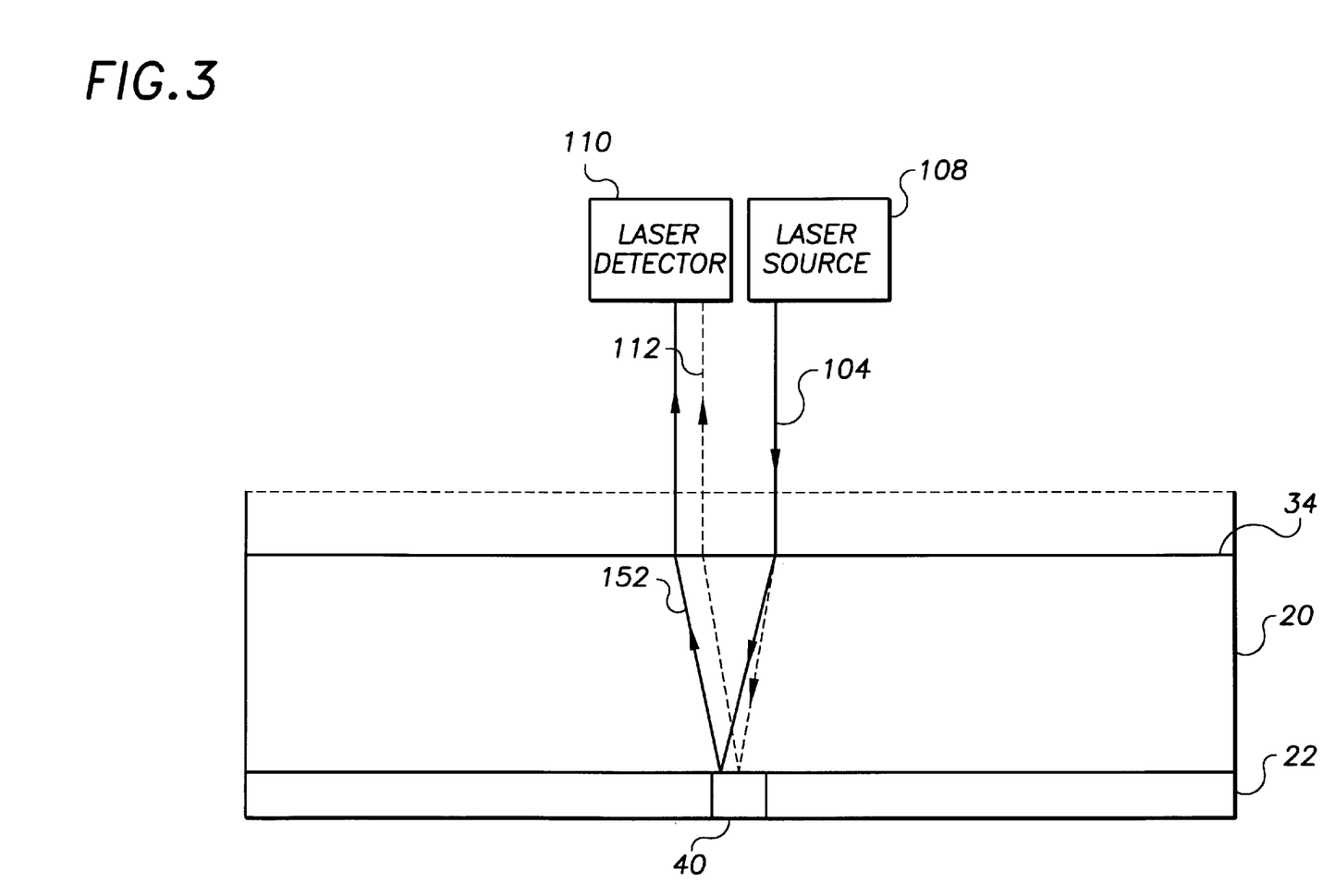
FIG. 3 is a cross-sectional view of a semiconductor structure undergoing laser analysis according to an example embodiment, the structure including a circuit having had selected test patterns applied thereto and halted in a selected state.

FIG. 3 is a cross-sectional view of an integrated circuit undergoing laser analysis according to an example embodiment. The integrated circuit is in a heated state, for example, after having had selected test patterns applied thereto and halted in a selected state. Heat generated from within the circuit as a result of the test patterns affects the index of refraction of the substrate 20. Thus, the reflected laser light 152 is phase shifted by the heated silicon. The change in the index of refraction changes the intensity of laser light reflected from the integrated circuit, as measured by detector 110. Most often the intensity appears to decrease. However, it has been observed that in some cases the intensity will increase. A heated area of substrate 20 will change the focus of the reflected laser light as compared to a lesser heated area. A change in focus is caused by a change in the index of refraction, which in turn is caused by a temperature change in an area of the circuit. As the temperature increases, more electron-hole pairs are present, thereby increasing the index of refraction. The change in the index of refraction is linearly related to the number of carriers.

The dashed lines represent an example path of the laser light through the substrate 20 at room-temperature or in a state in which no power is applied, such as that shown in FIG. 2. Because the laser detector 110 is focused on the reflected laser light 112, the detector 110 will not be focused on the reflected laser light 152 that follows a different path through the substrate 20. The lesser focus results in a lesser intensity level of detected laser light.

The laser analysis of the semiconductor structure may be performed for a selected location relative to the integrated circuit, or the analysis may involve scanning a selected area or the entire integrated circuit. The single location mode can be used where it is desired to observe the change in reflected laser light intensity for a selected point in the circuit.

The scan mode analysis is used to create a map of the reflected laser intensity levels for a selected portion of or the entire circuit. An area of the integrated circuit is laser scanned, and detected intensity levels are associated with respective x-y coordinates of the integrated circuit. The intensity levels are then compared to corresponding reference intensity levels. In comparing the measured intensity levels with reference intensity levels, conventional image processing techniques can be used to create an image, such as subtracting the reference intensity levels from the corresponding intensity levels of the integrated circuit undergoing analysis. In another example embodiment, an image can be created by dividing the intensity levels measured for the integrated circuit undergoing analysis by the corresponding reference intensity levels.

In an example embodiment, the invention generally supports static mode testing. That is, the laser scan occurs when the integrated circuit is in a steady state. Such a test can be useful when the integrated circuit is known to fail at a known point in a test pattern. The laser scan analysis is performed by first applying a selected test pattern to the integrated circuit, and at the point in the is test pattern where the integrated circuit is known to fail, the clock signal applied to the integrated circuit is stopped and voltage levels that are applied to the pins of the integrated circuit are maintained in a steady state. Then the laser scan is performed on the circuit to identify points or areas in the circuit that are hot.

Figure 4:
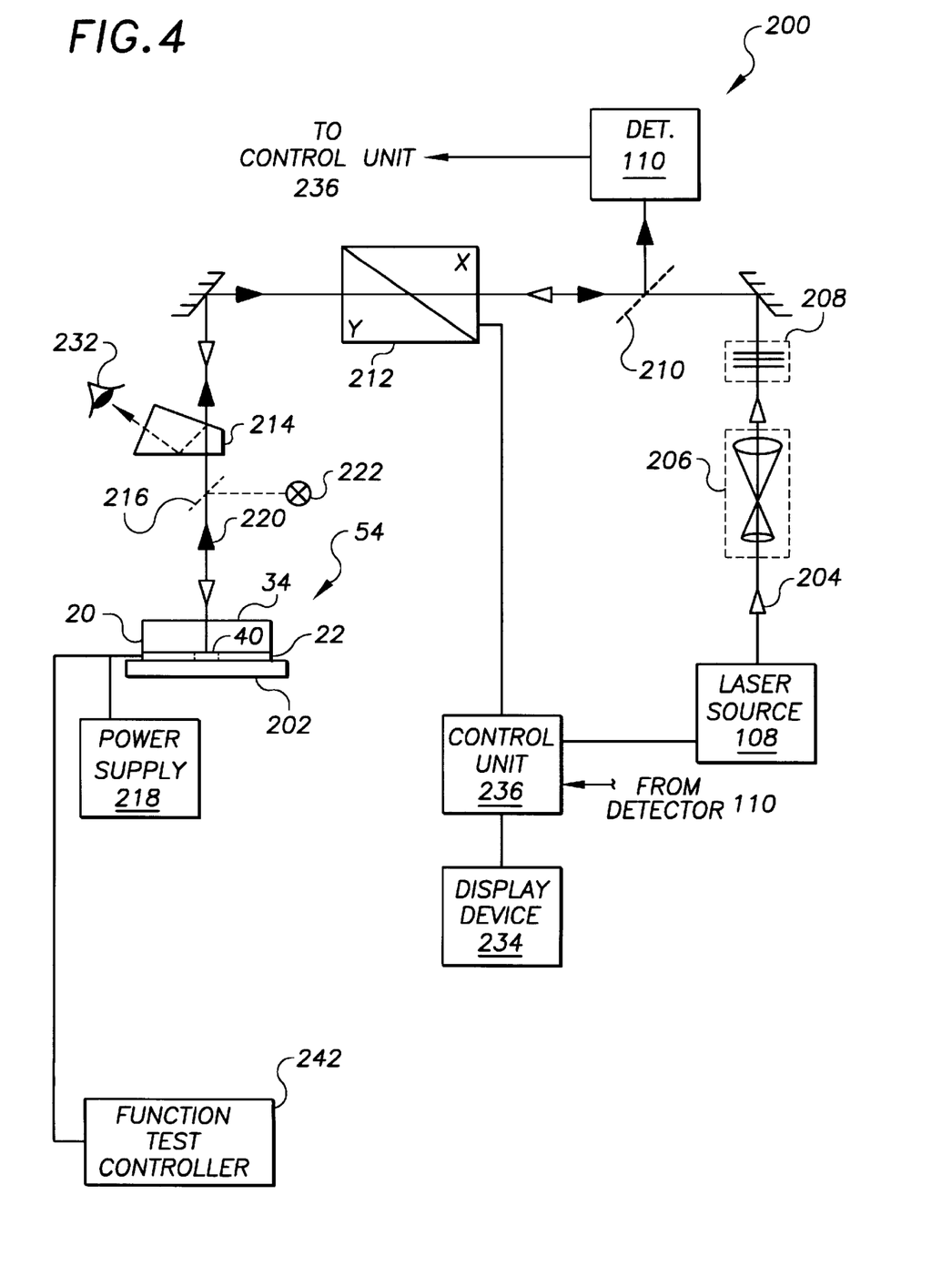
FIG. 4 is a block diagram of a system for laser analysis of a integrated circuit, according to an example embodiment of the invention.

FIG. 4 is a block diagram of a system 200 for laser analysis of an integrated circuit, according to an example embodiment of the invention. The system 200 is used both for establishing reference intensity levels of reflected laser light, as described above, and for measuring intensity levels of laser light for the integrated circuit undergoing analysis.

Semiconductor substrate 20 is positioned upon a holder 202 such that the backside surface 34 is exposed for analysis. Laser source 108 generates incident beam 204 as described above. Laser source 108 is, for example, a neodymuim:yttrium-aluminum-garnet (Nd:YAG) laser producing laser light having a wavelength of about 1064 nm in air. In another embodiment, the laser source 108 provides laser light having a wavelength of approximately 1300 nm, such as from a solid state diode or YAG laser. It will be appreciated that other near-infrared lasers are compatible with the present invention.

Incident beam 204 passes through beam expansion optics 206 which control the cross-sectional area (i.e., width) of incident beam 204, determining the illuminated area or "spot size" on the backside surface 34 substrate 20. Incident beam 204 then passes through attenuating filter 208 which controls the intensity of incident beam 204. Attenuating filter 208 operates such that incident beam 204 is given a predetermined intensity. The system also includes a first beam splitter 210 and a detector 110.

Incident beam 204 passes through first beam splitter 210 before entering an x-y deflecting unit 212. Deflecting unit 212 determines the position of the point of entry of incident beam 204 into the backside surface 34 of substrate 20 in order to illuminate portion 40 of circuit layer 22. Deflecting unit 212 permits the scanning of incident beam 204 across the backside surface 34 of substrate 20. Incident beam 204 then passes through a viewing lens 214 and a second beam splitter 216, striking the backside surface 34. Power supply 218 is coupled to circuit layer 22 and supplies electrical power to the integrated circuit within the circuit layer 22 during analysis.

Incident beam 204 enters the backside surface 34 of substrate 20, and exit beam 220 emerges from the backside surface as described above. A visible light source 222 produces visible light for viewing the backside surface 34 by a user. The second beam splitter 216 directs the visible light onto the same area or spot where incident beam 204 enters the backside surface 34. Visible light reflected from the backside surface 34 follows the same path as exit beam 220. The reflected visible light passes through second beam splitter 216 and into viewing lens 214. The viewing lens 214 directs the reflected visible light into the user's eye 232.

A display device 234 is coupled to a control unit 236, which in turn is coupled to the laser source 108 and to the x-y deflecting unit 212. Control unit 236 directs deflector 212 to scan incident beam 204 across the substrate 20 in one embodiment. In another embodiment, control unit 236 directs the deflector 212 to direct the incident beam 204 at a selected point on the backside surface 34 of the substrate 20. Control unit 236 may be a computer system, for example.

The control unit 236 is also coupled to detector 110. Detector 110 can be a photo-diode or photo-voltaic detector in two example embodiments. Exit beam 220 follows the same path as incident beam 204, passing through second beam splitter 216, viewing lens 214, and deflecting unit 212. The first beam splitter 210 directs exit beam 220 toward detector 110. Control unit 236, in one embodiment, directs deflecting unit 212 to scan incident beam 204 across the backside surface 34. In this embodiment, detector 110 produces an output signal indicative of the intensity of exit beam 220. Control unit 236 receives the output signal produced by detector 110 and generates a two-dimensional image of the electronic components within the circuit layer 22. Display device 234 receives the output signals from the control unit 236 and visually displays the two-dimensional image of the components.

A function test controller 242 is coupled to circuit layer 22. The function test controller 242 is used to input test patterns to the integrated circuit and provide control signals for placing the circuit in a desired operational state prior to laser analysis.

Hardware may be required to keep the heat from the integrated circuit from diffusing. For example, a cover or lid that is adapted to conform to the dimensions of the device may be desirable. The cover permits exposure of the backside of the substrate to the laser scanning equipment while slowing diffusion of heat from the integrated circuit. Example covers are provided as "thermal solutions" by Schlumberger Limited. It will be appreciated that such example thermal solutions may require adaptation for mounting on hardware compatible with example laser scanning systems, such as those available from Schlumberger.

Figure 5:
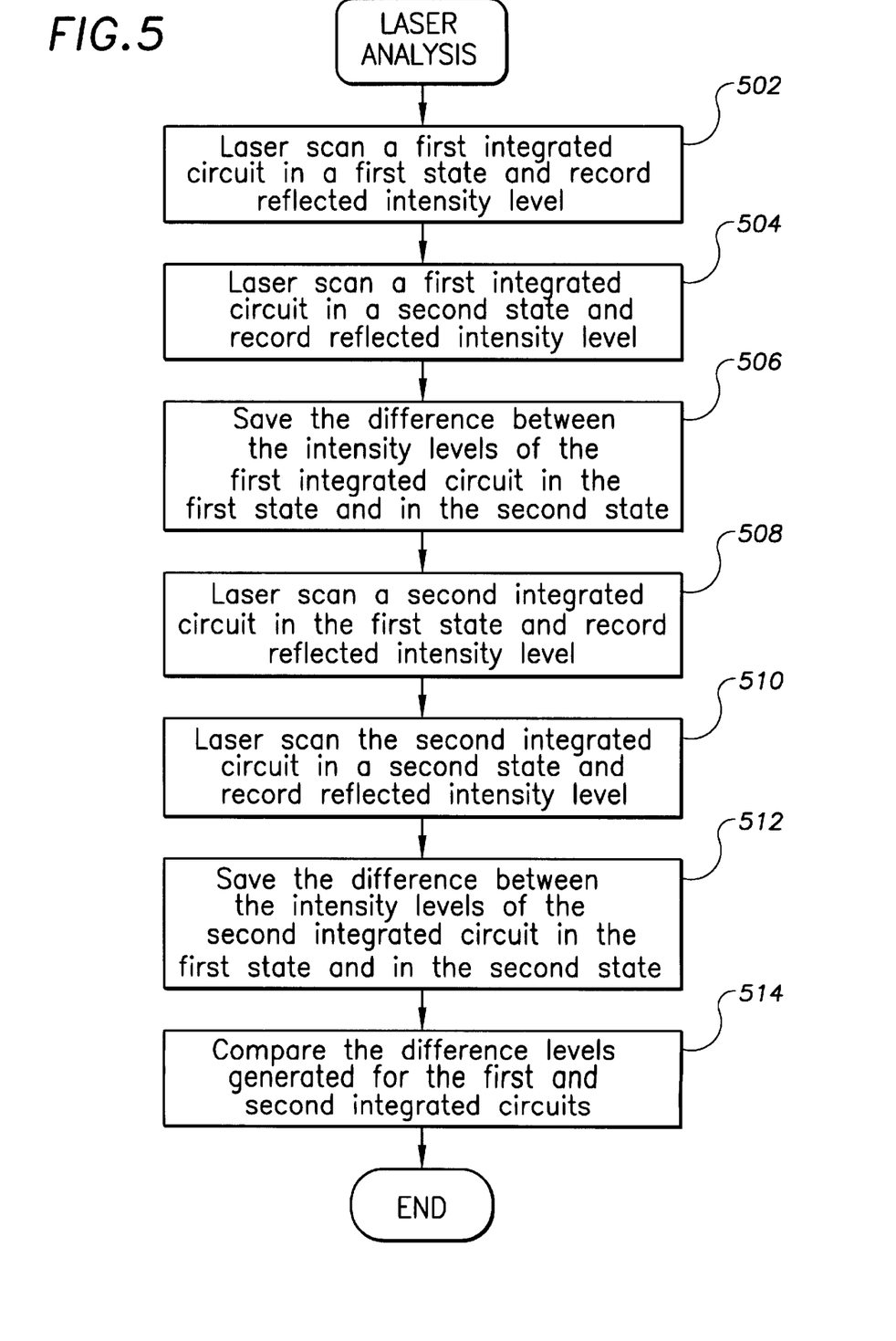
FIG. 5 is a flowchart of a method for analyzing temperature characteristics of an integrated circuit according to an example embodiment of the invention.

FIG. 5 is a flowchart of a method for analyzing temperature characteristics of an integrated circuit according to an example embodiment of the invention. At block 502, a first integrated circuit is subjected to a laser scan where the first integrated circuit is in a first state. For example, the first integrated circuit may be a known functional integrated circuit that is laser scanned at room temperature with no power applied. The intensity levels of the reflected laser light are recorded during the scan.

The first integrated circuit is then subjected to a second laser scan at block 504. However, before the second laser scan, the first integrated circuit is put into a second state. For example, the second state could comprise the circuit having power applied thereto and having had performed a selected set of test vectors. The intensity levels of the reflected laser light are then recorded during the second laser scan.

At block 506, a first difference level is computed between the intensity levels associated with the first state and the intensity levels associated with the second state. Conventional image processing techniques can be used to obtain the first difference level.

As shown by blocks 508, 510, and 512, the above-described process steps are repeated for a second integrated circuit, for example, the integrated circuit to be analyzed. At block 514, the difference levels associated with the first and second integrated circuits are compared. If the first difference level exceeds the second difference level by a selected value, there may be a defect in the circuit. It will be appreciated that the selected value may be derived from running a series of tests for a batch of integrated circuits that are known to be bad.

As noted above, the present invention is applicable to a number of different semiconductor structures and arrangements. Accordingly, the present invention should not be considered limited to the particular examples described above, but rather should be understood to cover all aspects of the invention as fairly set out in the attached claims. Various modifications, equivalent systems, as well as numerous structures to which the present invention may be applicable will be readily apparent to those of skill in the art upon review of the present specification. The claims are intended to cover such modifications and devices.

What is claimed is:

1. A method for analyzing temperature characteristics of an integrated circuit having internal circuitry in a region opposite a back side, comprising:
    directing a beam of laser light at a back side of the integrated circuit;
    measuring an intensity level of laser light reflected from a target region including the circuitry in the integrated circuit; and
    comparing the intensity level with a reference intensity level and, in response, obtaining a temperature characteristic of the integrated circuit.

2. The method of claim 1, wherein comparing the intensity level with a reference intensity level and, in response, obtaining a temperature characteristic of the integrated circuit includes detecting a magnitude of difference between the reference intensity level and the intensity level of the reflected laser light.

3. The method of claim 1, wherein the laser light is generated from a near-infrared type laser.

4. The method of claim 1, wherein an angle of incidence of the beam of laser light the integrated circuit is substantially perpendicular.

5. The method of claim 1, wherein an angle of incidence of the beam of laser light with the integrated circuit is between about 30° and 45°.

6. A method for analyzing temperature characteristics of an integrated circuit, comprising:
    directing laser light at a back side of a first integrated circuit having internal circuitry in a target region opposite the back side;
    establishing a reference intensity level from laser light reflected from the target region including circuitry in the first integrated circuit;
    directing laser light at a back side of a second integrated circuit having internal circuitry in a target region opposite the back side;
    establishing a second intensity level from the laser light reflected from the target region including circuitry in the second integrated circuit; and
    comparing the reference intensity level to the second intensity level, whereby a magnitude of difference between the reference and second intensity levels indicates a temperature characteristic for the second integrated circuit relative to the first integrated circuit.

7. The method of claim 6,
    wherein the step of establishing the reference intensity level comprises steps (a)–(c);
    (a) measuring a first intensity level of laser light directed at a target region having circuitry via the back side of a first integrated circuit and reflected therefrom, the first integrated circuit being in a first state;
    (b) measuring a second intensity level of laser light directed at a target region having circuitry via the back side of a first integrated circuit and reflected therefrom, the first integrated circuit being in a second state; and
    (c) establishing a first delta value of the difference between the first intensity level and the second intensity level associated with the first integrated circuit; and
    wherein the step of establishing the second intensity level comprises steps (d)–(f);
    (d) measuring a first intensity level of laser light directed at a target region having circuitry via the back side of a second integrated circuit and reflected therefrom, the second integrated circuit being in a first state;
    (e) measuring a second intensity level of laser light directed at a target region having circuitry via the back side of a second integrated circuit and reflected therefrom, the second integrated circuit being in a second state; and
    (f) establishing a first delta value of the difference between the first intensity level and the second intensity level associated with the second integrated circuit.

8. The method of claim 7, wherein the first state for the first and second integrated circuits comprises no power applied to the first and second integrated circuits, and the second state for the first and second integrated circuits comprises a selected power level applied to the first and second integrated circuits.

9. The method of claim 7, wherein the laser light is generated from a near-infrared type laser.

10. The method of claim 6, wherein an angle of incidence of the beam of laser light with surfaces of the first and second integrated circuits is substantially perpendicular.

11. The method of claim 6, wherein an angle of incidence of the beam of laser light with surfaces of the substrates is between about 30° and 45°.

12. A method for analyzing temperature characteristics of an integrated circuit, comprising:
   (a) scanning a first integrated circuit with a beam of laser light, the first integrated circuit being in a state in which no power is applied;
   (b) measuring a first intensity level of laser light reflected from a target region having circuitry in the first integrated circuit;
   (c) supplying voltage and current to the first integrated circuit;
   (d) running a selected series of test vectors on the first integrated circuit;
   (e) measuring a second intensity level of laser light reflected from the target region having circuitry in the first integrated circuit;
   (f) establishing a delta value of a difference between the first and second intensity levels;
   repeating steps (a)–(f) using a second integrated circuit instead of the first integrated circuit;
   comparing the delta value of the first integrated circuit to the delta value of the second integrated circuit whereby a magnitude of difference between the delta values indicates a temperature characteristic for the second integrated circuit relative to the first integrated circuit.

13. The method of claim 12, wherein the laser light is generated from a near-infrared type laser.

14. The method of claim 12, wherein an angle of incidence of the beam of laser light with the first and second integrated circuits is substantially perpendicular.

15. The method of claim 12, wherein an angle of incidence of the beam of laser light with the first and second integrated circuits is between approximately 30° and 45°.

16. The method of claim 12, further comprising placing a cover over the substrate the electronic circuit to reduce diffusion of heat generated by the circuit.

17. The method of claim 12, wherein the beam of laser light is directed at back sides of the first and second integrated circuits.

18. A method for analyzing circuitry in an integrated circuit device having internal circuitry in a region opposite a back side, the method comprising:
   directing a beam of laser light at a target region including the circuitry via a back side of the integrated circuit device; and
   detecting a temperature characteristic of the integrated circuit device as a function of laser light reflected from the target region; and
   analyzing the integrated circuit device based upon said temperature characteristic.

19. A system for analyzing circuitry in an integrated circuit die having internal circuitry in a region opposite a back side, the system comprising:
   means for directing a beam of laser light at a target region including the circuitry via a back side of the integrated circuit;
   means for detecting a temperature characteristic of the integrated circuit as a function of laser light that is reflected from the target region; and
   means for analyzing the integrated circuit based upon said temperature characteristic.

20. A system for analyzing temperature characteristics of an integrated circuit die having internal circuitry in a region opposite a back side, comprising:
   a laser source configured to direct a beam of laser light at a target region including the circuitry via a back side of the integrated circuit;
   a detector arrangement configured to detect a temperature characteristic of the integrated circuit as a function of laser light that is reflected from the target region; and
   an analyzer for analyzing the integrated circuit based upon said temperature characteristic.

21. The system of claim 20, wherein the laser source is adapted to generate near-infrared laser light.

22. The system of claim 20, wherein the laser source includes a laser scanning microscope.

23. The system of claim 20, wherein the detector arrangement includes an IR microscope.

24. The system of claim 20, wherein the detector arrangement includes a comparator adapted to compare an intensity level of the reflected laser light to a reference intensity level.

25. The system of claim 20, further comprising a power supply adapted to apply selected electrical test patterns to the integrated circuit die.

* * * * *